(12) United States Patent
Bansal et al.

(10) Patent No.: US 10,816,442 B2
(45) Date of Patent: Oct. 27, 2020

(54) REMOTELY MONITORED GREENHOUSE GAS FLUX TESTING OF WETLANDS AND VEGETATION

(71) Applicant: The U.S.A., as represented by the DOI, Washington, DC (US)

(72) Inventors: Sheel Bansal, Jamestown, ND (US); Peter Gould, Olympia, WA (US)

(73) Assignee: U.S. Geological Survey, Reston, VA (US)

( * ) Notice: Subject to any disclaimer, the term of this patent is extended or adjusted under 35 U.S.C. 154(b) by 300 days.

(21) Appl. No.: 16/052,577

(22) Filed: Aug. 1, 2018

(65) Prior Publication Data
US 2020/0041388 A1  Feb. 6, 2020

(51) Int. Cl.
| | | |
|---|---|---|
| *G01N 1/22* | (2006.01) | |
| *B25J 9/16* | (2006.01) | |
| *G01N 33/00* | (2006.01) | |
| *G01N 1/26* | (2006.01) | |
| *G01N 1/00* | (2006.01) | |

(52) U.S. Cl.
CPC .......... *G01N 1/2294* (2013.01); *B25J 9/1664* (2013.01); *G01N 1/26* (2013.01); *G01N 33/0075* (2013.01); *G01N 2001/002* (2013.01)

(58) Field of Classification Search
CPC .... G01N 1/2294; G01N 1/26; G01N 33/0075; G01N 2001/002; G01N 2001/2285; G01N 2001/2291; B25J 9/1664
USPC .................. 73/23.2, 863.01, 864.31, 864.91
See application file for complete search history.

(56) References Cited

U.S. PATENT DOCUMENTS

| | | | |
|---|---|---|---|
| 7,509,836 B2 | 3/2009 | Johnson | |
| 8,712,692 B2 | 4/2014 | Risk | |
| 2002/0090320 A1* | 7/2002 | Burow | G01N 35/0099 422/64 |
| 2009/0301234 A1 | 12/2009 | Risk | |
| 2010/0294046 A1* | 11/2010 | Boeke | C12M 33/07 73/863.01 |
| 2016/0144506 A1* | 5/2016 | Natsume | B25J 9/1661 700/250 |

* cited by examiner

*Primary Examiner* — Benjamin R Schmitt
(74) *Attorney, Agent, or Firm* — James Mitchell; Jill Welytok

(57) ABSTRACT

In various embodiments, the invention is a versatile, automated system to allow researchers to continuously measure gas flux rates from multiple chambers over time without (or with reduced) need for personnel in the field. The invention is compatible with any high-frequency analyzer or vial filler and most chamber designs.

20 Claims, 5 Drawing Sheets

REMOTELY MONITORED GREENHOUSE GAS FLUX TESTING OF WETLANDS AND VEGETATION

FIELD OF INVENTION

This invention relates to the field of sampling gases emitted from soil or bodies of water.

BACKGROUND OF THE INVENTION

The U.S. Geological Survey (USGS) is a bureau of the Department of the Interior with a mission to study and protect the earth's resources. USGS is the nation's preeminent earth science research agency. Pursuant to its mission, USGS scientists have collaborated with private manufacturers to develop technology to monitor greenhouse gas (GHG) emissions, and in particular emissions from wetlands.

Wetlands "sequester" GHG and prevent it from entering the atmosphere. Wetlands are viewed by scientists as critical for ameliorating the increase in GHG concentrations in the atmosphere and slowing the rate of global warming. Healthy wetland vegetation has the potential to absorb large amounts of carbon dioxide ($CO_2$) through photosynthesis. At the same time, wetlands also emit methane (CH4) to the atmosphere, which is a potent GHG in its ability to trap heat.

Currently, scientists rely on static-chamber methods to monitor GHG emitted from soil and water.

Static-chamber method studies require scientists or trained technicians to gather samples by placing chambers smaller than 1 $m^2$ on the soil surface at ten-meter intervals to trap gas samples over a thirty- to sixty-minute period and transfer the samples to serum vials on a daily or weekly basis for several weeks or months.

Once collected, the gas concentrations in the samples are analyzed in a lab using a gas chromatograph/mass spectrometer to determine the rate of changes in GHG concentrations over time, the flux rate.

There are several problems known in the art with respect to static-chamber testing methods.

Static-chamber testing methods are costly to deploy on site, often requiring human intervention over several weeks or months.

Static chamber testing methods do not produce consistent results because of deviations in GHG due to variation in soil topography, irregularities in height or size of vegetation and weather conditions, which can cause statistical anomalies. For this reason, chamber testing is unreliable for upscaling GHG over space and time. Moreover, current testing methods are not sufficiently versatile to test both soil and water during a testing period.

USGS researchers have identified a need for inexpensive in-situ testing equipment and protocols which can be readily adapted for a variety of testing environments to reduce anomalies.

USGS scientists have endeavored to produce a GHG monitoring apparatus to produce an increased number of reliable data sets for research and regulatory purposes and upon which the Environmental Protection Agency and other government agencies can rely to routinely test the impact of the widest possible range of GHG producing activities.

There have been attempts in the art to automate sampling and to enable remote monitoring. Robotic testing devices are known in the art, such as the devices produced by Li-Cor Biosciences ("Li-Cor") or Eosense. Li-Cor produces testing devices which couple sampling chambers with by robotic arms which move along a specific path at specified intervals. However, the Li-Cor system is limited to taking measurements on relatively flat soil and cannot accommodate the presence of tall vegetation or wetlands. Moreover, these systems require the purchase of a highly specialized gas analyzer that can test for only certain gases.

There is an unmet need for an unmanned, remotely monitored testing station.

There is an unmet need for devices that do not require the purchase of costly analyzers, and that can be adapted to use any analyzer and measure any terrain or body of water.

There is a further unmet need for a standardized, low-cost phase II testing method that can be easily implemented.

SUMMARY OF THE INVENTION

A greenhouse gas sampling apparatus comprised of at least one selectively attachable chamber, at least one robotic arm assembly, wherein each selectively attachable chamber is operatively coupled with one robotic arm assembly, a robotic arm controller which controls the movement of the robotic arm assembly, a plurality of valves that each discharge into a central manifold and are controlled by a valve controller, a testing system component which is operationally coupled with the central manifold, and a user interface.

TERMS OF ART

As used herein the term "analyzer" means any device used to measure the concentration of a gas.

As used herein, the term "chamber type selection criteria" includes, but is not limited to: chamber dimensions, material, sample aperture dimensions, number of outlet apertures, outlet aperture dimensions, and number of inlet apertures.

As used herein, the term "conveyance valve" means a valve that is opened and closed to control the flow of gas.

As used herein, the term "flux" means the change in atmospheric gas concentration associated with landscapes or waterscapes.

As used herein, the term "GHG analyzer" means an analyzer calibrated to measure the concentration of a greenhouse gas, including but not limited to methane, carbon dioxide, and nitrous oxide.

As used herein, the term "sampling aperture" means an opening at bottom of the sampling chamber that allows gas emitted from the land or water sample to rise into the chamber when the chamber is in the testing position.

DETAILED DESCRIPTION OF THE INVENTION

Figure 1A:
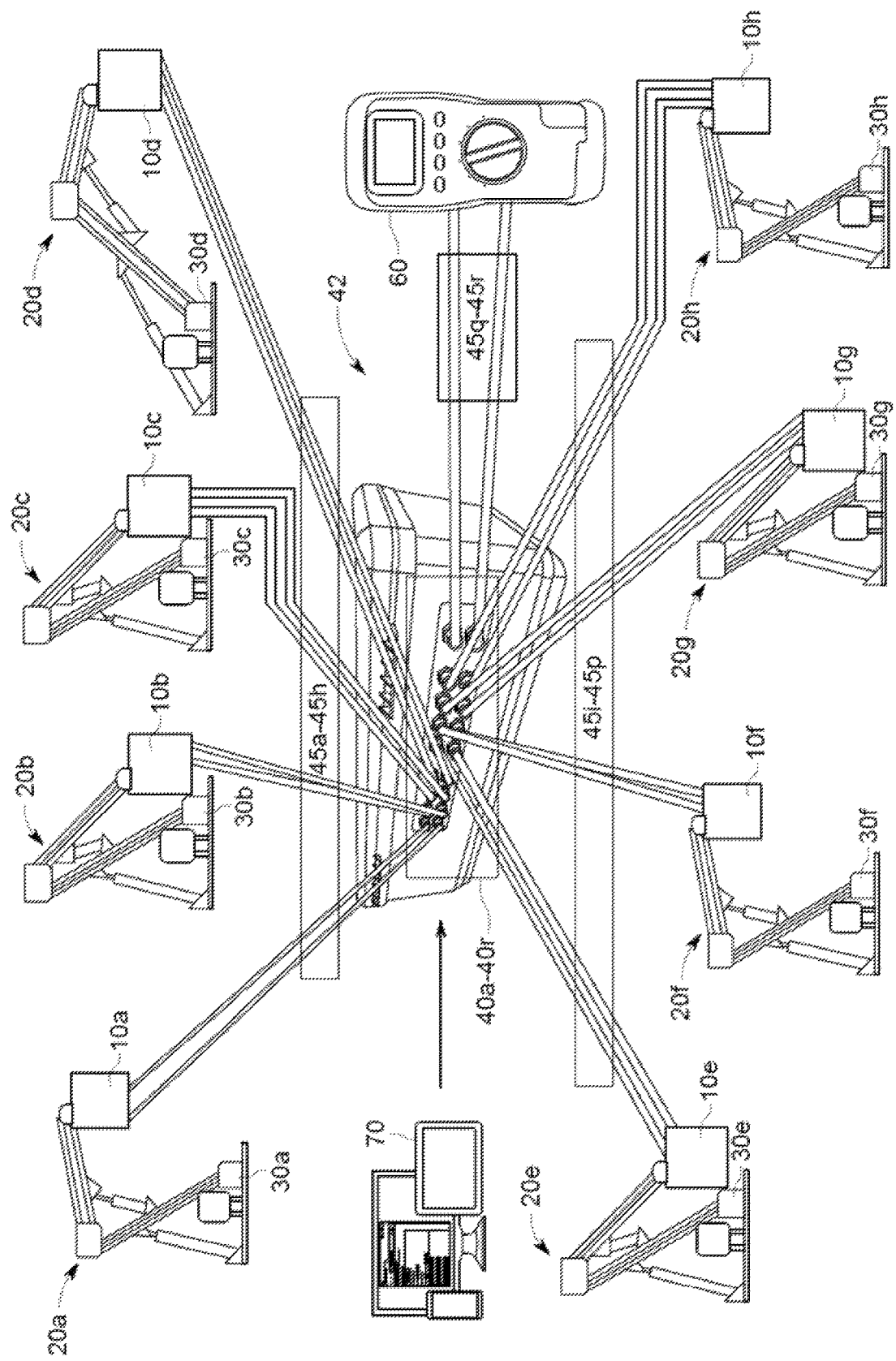
FIG. 1A illustrates an exemplary embodiment of a modular automated greenhouse gas emissions sampling system in use with a gas analyzer component.

FIG. 1A illustrates an exemplary embodiment of modular automated greenhouse gas emissions sampling system 100 in use with a gas analyzer component. The elements depicted in FIG. 1 include a plurality of selectively attachable chambers 10a through 10h, plurality of robotic arm assemblies 20a through 20h, robotic arm controller 30, plurality of gas conducting apertures 40a through 40r, inlet and outlet tubing pairs 45a through 45r, testing system component 60, and user interface 70.

In the embodiment shown, selectively attachable chamber 10 has a sampling aperture at the bottom to allow gas to rise into chamber 10. In the exemplary embodiment shown, each selectively attachable chamber 10 is attached to robotic arm assembly 20 and robotic arm assembly 20 will move chamber 10 through alternating cycles of testing positions where a sampling aperture at the bottom of the chamber is positioned directly above sampling area of the ground or water that is emitting gases, and resting positions where the chamber is raised to have distance between the sampling aperture and the ground or water being monitored. In the exemplary embodiment shown, the term sampling area is an area of terrain that can be sampled by the chamber, with the dimensions of the sampling aperture of chamber 10.

In various embodiments, selectively attachable chambers 10 include sampling apertures at the bottom of the chamber through which greenhouse gas emissions enter chamber 10, and outlet apertures near the top of the chamber through which greenhouse gas emissions enter tubing 45 and move toward gas conducting aperture 40. In various embodiments, selectively attachable chambers 10 may also include inlet apertures that receive gas from gas conducting aperture 40, through tubing 45.

In various embodiments, robotic arm assembly 20 includes robotic arm controller 30, which has a microprocessor that stores the programmed movement path for robotic arm assembly 20. Robotic arm controller 30 receives a signal from valve controller 50 to actuate movement of robotic arm assembly 20, according to a programmed movement path.

In various embodiments, robotic arm assembly 20 moves chamber 10 horizontally, as well as vertically, to avoid obstacles and to allow the resting position to be as far as possible from the testing position. This avoids creating a change in temperature or rainfall in the sample area that would cause an experimental artifact. The movement path of robotic arm assembly 20 can be adapted to the test site environment. For example, if the sample area is in a bog or wet area, the base of robotic arm assembly 20 can be put on a floating dock and then robotic arm assembly 20 can reach over the edge of the dock down to the water surface.

In various embodiments, robotic arm assembly 20 can place chamber 10 in multiple testing positions and chamber 10 is not limited to one testing position. In various embodiments, robotic arm assembly 20 can rotate 360 degrees to place chamber 10 in multiple testing positions.

In the exemplary embodiment shown, only one chamber 10 will be in a testing position at any given time. In various embodiments, testing positions may vary between cycles, meaning that a given chamber does not need to be returned to the same testing position for every cycle of the testing session.

System 100 can use any shape chamber, which allows it to measure gas flux from any agriculture field, wetland, forest, prairie, peatland, aquatic environment, or other terrain. In the exemplary embodiment shown, chamber 10 is attached to robotic arm assembly 20 by four bolts. In alternative embodiments, chamber 10 is attached to robotic arm assembly 20 by wing bolts to facilitate removal and replacement of chamber 10.

In the exemplary embodiment shown, the user selects chamber 10 based on the sampling environment. Chambers have structural parameters including chamber dimensions, sample aperture dimensions, number and size of outlet apertures, number of inlet apertures, and transparency and weight of material. Chamber 10 may be made of acrylic, metal, PVC, and other rigid materials. Ideally, chamber 10 will not interfere with plant growth so the natural environmental conditions are not changed, avoiding negative impact on the validity of the test results.

The required dimensions and characteristics of chamber 10 may be determined by testing site characteristics, including terrain, soil moisture saturation level, and density of plant cover on the terrain. The presence of plants, size of plants, expected rate of GHG flux, and variation of terrain being tested determines the dimensions and characteristics required for chamber 10. If plants are present, the user will select taller, transparent chambers to avoid interfering with plant growth. If the terrain has a lot of variation per square foot, then the user will select chamber 10 with a larger sampling aperture. If the expected GHG flux rate is low, then the user will select a shorter chamber.

In the exemplary embodiment shown, robotic arm controller 30 controls the movement of each robotic arm assembly 20. In various embodiments, robotic arm assembly 20 includes at least one accelerometer to monitor and report the movements of robotic arm assembly 20 and to ensure accurate placement of operatively coupled selectively attachable chamber 10. In various embodiments, robotic arm assembly 20 includes sensors to detect animals, growing plants, or other moving obstacles to adjust the movement path of robotic arm assembly 20 or send a warning to the user if the path cannot be adjusted. In various embodiments, robotic arm assembly 20 includes sensors to detect if robotic arm assembly 20 is improperly leveled or balanced, in order to send a warning to the user. These features all facilitate remote monitoring of system 100.

In various embodiments, system 100 includes a data transmitter to send data in real time via a wireless network. The user can remotely monitor this data transmission to detect if the system has stopped collecting or transmitting data for any reason.

In various embodiments, selectively attachable chambers 10 also include one or more sensor components attached to the interior of the chamber or a mechanism for circulating air inside of the chamber, including a fan. The interior sensor components may sense and/or measure the presence of chemicals, atmospheric temperature, atmospheric pressure, soil moisture levels, relative humidity, and light intensity levels. In various embodiments, the sensors or air circulation components are powered by the robotic arm power source.

In the exemplary embodiment shown, each selectively attachable chamber 10 has an outlet aperture that is operatively coupled with one gas conducting aperture 40 by a length of tubing 45 to conduct gas from the chamber to conveyance valve 44. The connection at each end of tubing 45 is air-tight. In various embodiments, each selectively attachable chamber 10 also has an inlet aperture that is operatively coupled with one gas conducting apertures 40 by length of tubing 45 to allow gas to recycle back into chamber 10. Gas conducting apertures 40 conduct gas into or out of central manifold 42. In various embodiments, tubing 45 is Teflon tubing.

Testing system component 60 has an inlet aperture that is operationally coupled with central manifold 42. Testing system component 60 may be a gas analyzer that analyzes gas samples in real time or an automated system that fills vials with the gas samples for later analysis in a laboratory. In the exemplary embodiment shown, testing system component 60 is a gas analyzer that has an inlet aperture operationally coupled to gas conducting aperture 40q and an outlet aperture operationally coupled to gas conducting aperture 40r. This outlet aperture allows gas to return from testing component 60 to chamber 10 after it is analyzed. In various embodiments, the gas analyzer measures atmospheric gases including but not limited to carbon dioxide, methane, or nitrous oxide and may be a gas analyzer known in the art. In various embodiments, the gas analyzer measures a gas which absorbs and emits radiant energy within the thermal infrared range, including but not limited to gases that occur naturally in the atmosphere, such as water vapor, carbon dioxide ($CO_2$), methane ($CH_4$), and nitrous oxide ($N_2O$), and those that are man-made, such as chlorofluorocarbons (CFCs), hydrofluorocarbons (HFCs), and perfluorocarbons.

In various embodiments, the gas analyzer may have a data transmission component to transfer data to a remote user to assist in monitoring the system remotely, in real time. The data transfer may occur wirelessly.

In the exemplary embodiment shown, the passage of gas through gas conducting apertures 40 is controlled by conveyance valves 44 to ensure that gas from only one chamber 10 in a testing position is conducted to testing system component 60 at any given time.

User interface 70 allows the user to input the desired locations for the testing and resting positions of the chambers, and the desired timing (chamber sampling order, sampling frequency, and sampling duration), which determines the instructions for robotic arm controller 30 and conveyance valve controller 50. In various embodiments, conveyance valve controller 50 is a virtual processing component configured to execute software instructions to mechanically open and close conveyance valves 44. In various embodiments, user interface 70 can allow the user to control apparatus 100 from any mobile device with Wi-Fi capability. In various embodiments, the software allows user-defined chamber timing, Wi-Fi communication with conveyance valve controller 50, cellular upload capability, and logs time stamp for easy integration with analyzer data.

In various embodiments, system 100 stores and transmits the following data: a timestamp, the robotic arm's identifier (for example, a name such as "wetland 7") and a code indicating whether the arm moved successfully or encountered a fault. When the robotic arm moves from the resting position to the sampling position, it sends a message back to conveyance valve controller 50 to indicate it was successful. In various embodiments, the robotic arm assembly includes an accelerometer. In various embodiments, the robotic arm assembly can sense whether it is in the correct position and how long it took to move there. If it is unable to reach the sampling position then it sends a fault signal back to conveyance valve controller 50.

In various embodiments, system 100 includes a memory storage component.

Because automated system 100 does not require manual sampling, it allows a single user to sample more frequently and from more sampling areas, increasing temporal and spatial resolution of samples. This will improve field measurements and increase sample integrity and sample size. In both circumstances, a more accurate measure of flux rates from increased spatial and temporal resolution is more accurate for calibrating models. This is especially important for flux rates of gases such as nitrous oxide, which spike within hours of a rain event and then decline exponentially.

In addition, because automated system 100 does not require manual sample collection, it will allow researchers to capture gas fluxes over a 24-hour period (diurnal data) more effectively, improving model predictions.

In various embodiments, user interface 70 receives user defined arm movement parameters to modify instructions implemented by robotic arm controller 30.

In various embodiments, user interface 70 receives user defined conveyance valve control parameters to modify instructions implemented by conveyance valve controller 50.

In various embodiments, user interface 70 receives user defined collection test parameter input to create testing session objects.

In various embodiments, user defined test parameter input includes total distance traveled by chamber 10 d, elevation y, distance x, uniform sampling interval T1, uniform sampling duration interval T2, detected gas type, gas source, chamber characteristics, test site characteristics, and test site terrain.

In various embodiments, testing session objects are virtual processing components that define chamber movement paths corresponding to user defined test parameter input.

In various embodiments, system 100 includes a database that stores and allows the user to access testing objects with software instructions for robotic arm controller 30 and conveyance valve controller 50.

In various embodiments, testing session objects define sampling intervals, sampling duration, chamber type selection criteria, and test session duration.

In various embodiments, user inputs include programmed paths of movement for robotic arm assembly 20, test session duration, time spent in testing position (sampling duration), time spent in resting position (sampling interval), chamber type selection criteria, and site terrain.

Figure 1B:
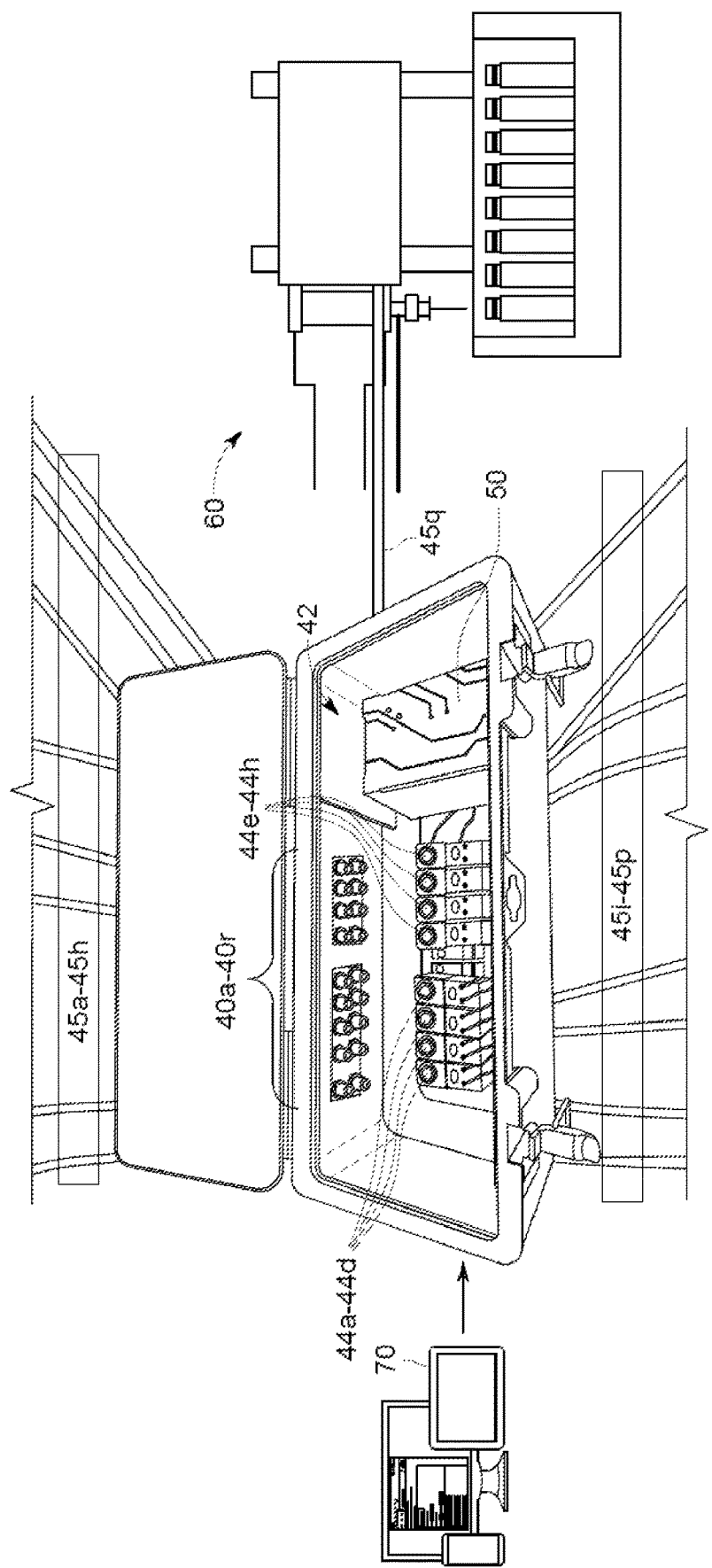
FIG. 1B illustrates an exemplary embodiment of a valve controller and solenoid valves in a central manifold.

FIG. 1B illustrates an exemplary embodiment of modular automated greenhouse gas emissions sampling system 100 in use with a vial collection component.

In the exemplary embodiment shown, testing system component 60 is an automated system that fills vials with the gas samples for later analysis in a laboratory. The vial filling component may be comprised of a pneumatic cylinder, a side-arm needle fitting, and a fraction collector.

In various embodiments, the user can collect the filled vials weekly and send to laboratory for analysis on a gas chromatograph/mass spectrometer (GC/MS). Estimating that the collection requires 2 hours of labor to conduct and each hour costs $50, this costs approximately $100/week.

In the exemplary embodiment shown, the passage of gas through gas conducting apertures 40 is controlled by conveyance valve controller 50, which opens and closes conveyance valves 44 to ensure that gas from only one chamber 10 in a testing position is conducted through central manifold 42 to testing system component 60 at any given time.

In various embodiments, the initial set-up of system 100 requires 16 hours of labor and costs approximately $800.

Figure 2:
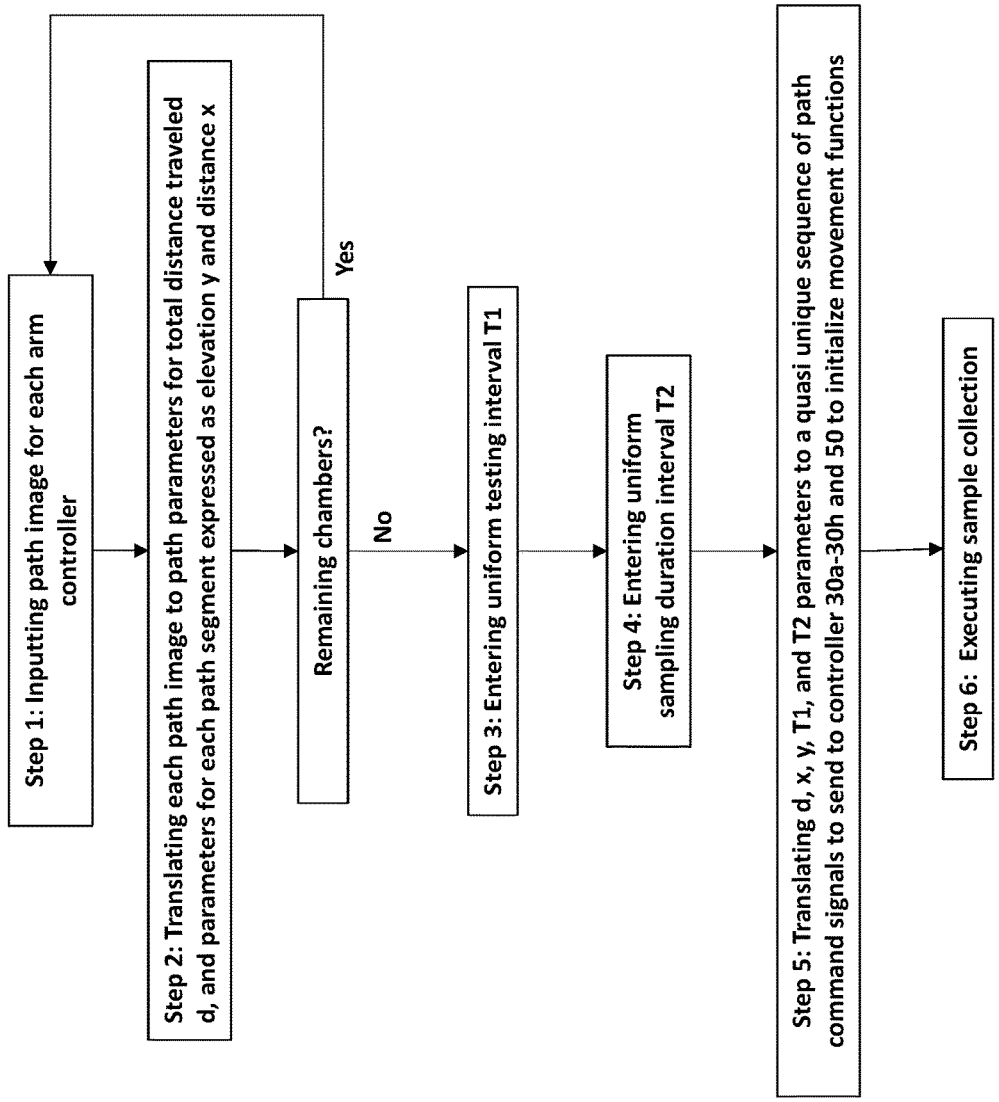
FIG. 2 illustrates an exemplary method for monitoring greenhouse gas flux.

FIG. 2 illustrates exemplary method 200 for monitoring greenhouse gas flux.

Step 1 is the step of inputting a path image for each arm controller.

The path image may be a movement path that corresponds to an image of the test site terrain.

Step 2 is the step of translating each path image to path parameters for total distance traveled d, and parameters for each movement path segment expressed as elevation y and distance x. This step is performed iteratively until all chamber paths are programmed.

Step 3 is the step of entering uniform sampling interval T1, which represents the length of time that a chamber is in the testing position.

Step 4 is the step of entering uniform sampling duration interval T2, which represents the length of time that a chamber is in the resting position.

Step 5 is the step of translating d, x, y, T1, and T2 parameters to a quasi-unique sequence of path command signals to send to controllers 30a-30h and/or 50 to initialize movement functions.

Collection parameters include the sampling position coordinates, the amount of time that each chamber will be in an active sampling position, the amount of time that each chamber will be in a resting position, and the sequence that determines which chamber is actively sampling.

Step 6 is the step of executing sample collection.

Figure 3:
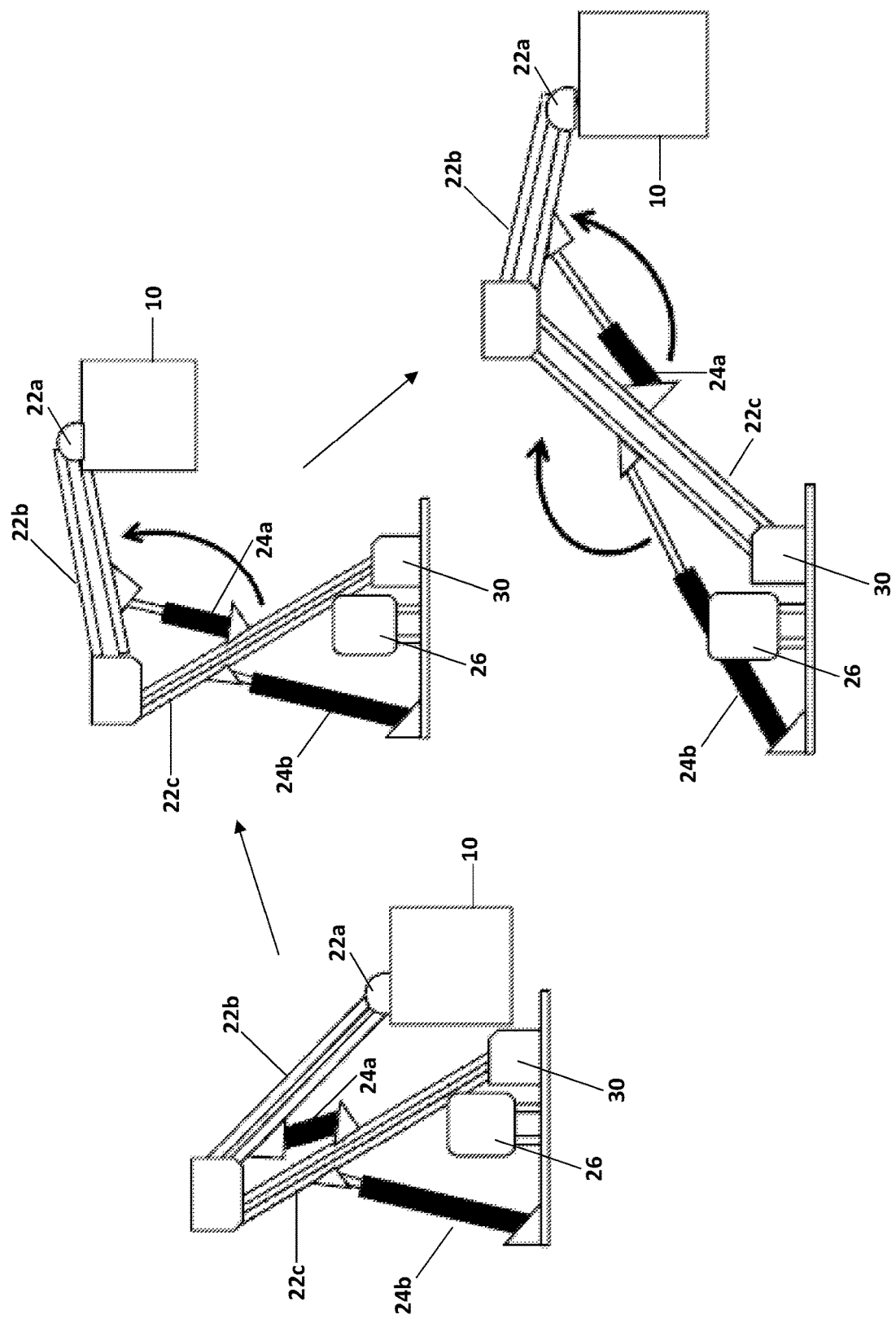
FIG. 3 illustrates an exemplary robotic arm assembly moving an operatively coupled selectively attachable chamber during use.

FIG. 3 illustrates exemplary robotic arm assembly 20 moving operatively coupled, selectively attachable chamber 10 during use.

In the exemplary embodiment shown, robotic arm assembly 20 includes pivotal segments 22a-c, mechanical actuators 24a-b, power source 26, and robotic arm controller 30.

In the exemplary embodiment shown, mechanical actuator 24 is a piston operationally coupled with pivotal segments 22, which receives a signal from robotic arm controller 30 to move pivotal segments 22.

Figure 4:
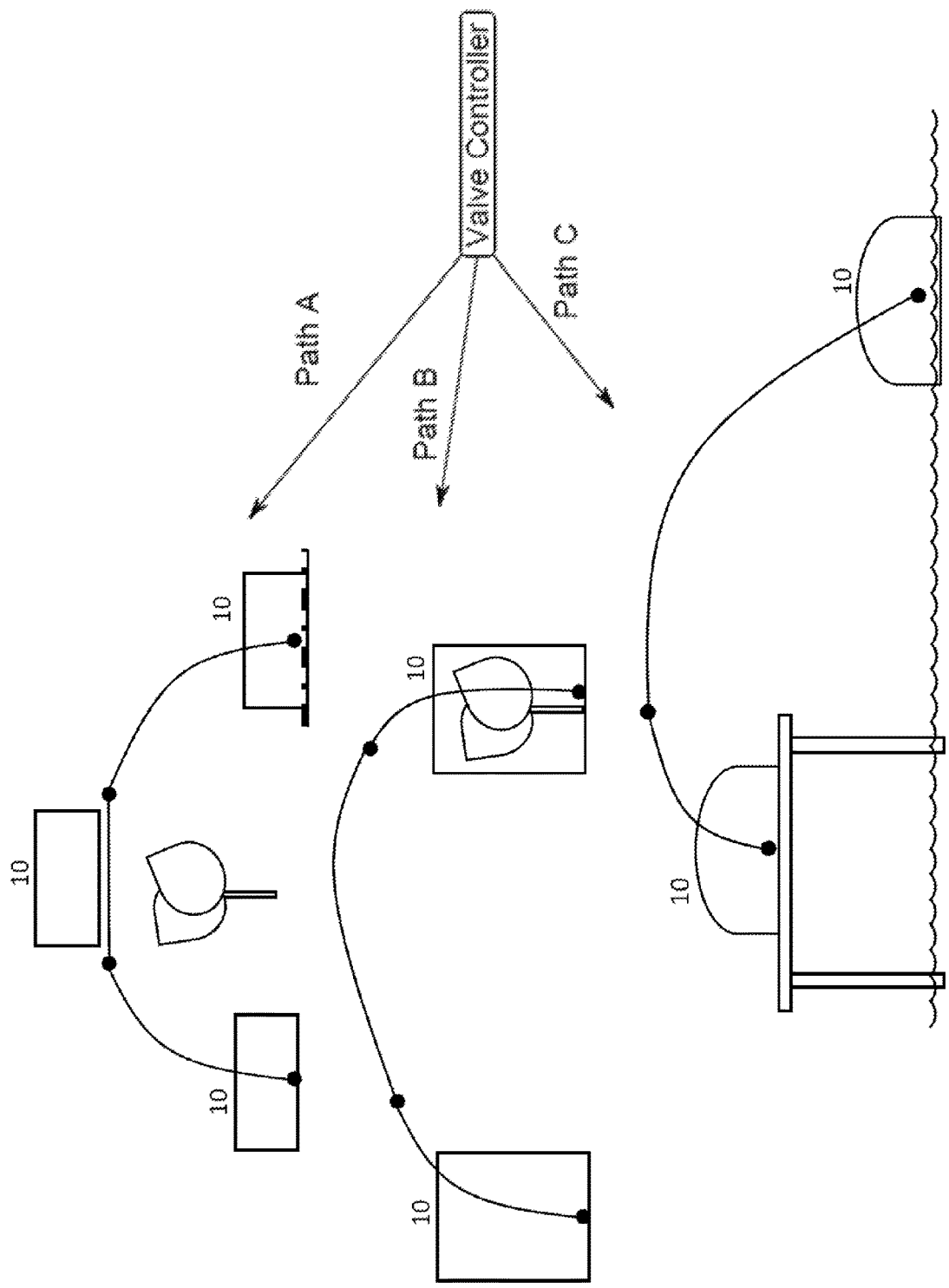
FIG. 4 illustrates exemplary movement paths of a selectively attachable chamber.

FIG. 4 illustrates exemplary movement paths of selectively attachable chambers 10.

In the exemplary embodiment shown, the movement path is represented by a line and path segments are represented by dots along the movement path.

In the exemplary embodiment shown, Path A shows the path of movement of selectively attachable chamber 10 from a resting position on the left, over a plant obstacle, to a testing position on the right, covering an area of short vegetation.

In the exemplary embodiment shown, Path B shows the path of movement of selectively attachable chamber 10 from a resting position on the left, to a testing position on the right, where the chamber is covering a tall plant in the testing position.

In the exemplary embodiment shown, Path C shows the path of movement of selectively attachable chamber 10 from a resting position on a floating dock on the left, to a testing position at a lower elevation on the right, over a body of water.

In the exemplary embodiment shown, the movement paths are transmitted by the valve controller to the robotic arm controller.

What is claimed is:

1. A greenhouse gas sampling apparatus comprised of:
a plurality of robotic arm assemblies;
a plurality of selectively attachable chambers, wherein each of said selectively attachable chambers is operatively coupled with one of said plurality of robotic arm assemblies;
a plurality of conveyance valves, wherein each of said plurality of conveyance valves is operatively coupled with one of said plurality of selectively attachable chambers;
one or more robotic arm controllers which control movement of said plurality of robotic arm assemblies; and
a conveyance valve controller.

2. The apparatus of claim 1, which is operatively coupled with a GHG analyzer.

3. The apparatus of claim 2, wherein said GHG analyzer includes a transmitter to transmit data in real time.

4. The apparatus of claim 1, which is operatively coupled with a gas sample collection system that collects gas samples in vials.

5. The apparatus of claim 1, wherein said conveyance valve controller is a virtual processing component configured to execute software instructions to mechanically open and close said plurality of conveyance valves.

6. The apparatus of claim 5, wherein said software instructions include parameters selected from a group consisting of: total distance traveled d, elevation y, distance x; uniform sampling interval T1, and uniform sampling duration interval T2.

7. The apparatus of claim 6, wherein said conveyance valve controller further includes a processing component for translating said d, x, y, T1, and T2 parameters to a quasi-unique sequence of path command signals to send to said one or more robotic arm controllers.

8. The apparatus of claim 7, wherein said conveyance valve controller further includes a processing component for initializing movement functions.

9. The apparatus of claim 8, wherein said conveyance valve controller further includes a processing component for executing sample collection.

10. The apparatus of claim 5, which further includes a central manifold operatively coupled with a GHG analyzer and only one of said plurality of selectively attachable chambers at any given time, based on said software instructions.

11. The apparatus of claim 1, wherein each of said plurality of selectively attachable chambers further includes one or more interior sensor components selected from a group consisting of: chemical sensors, temperature sensors, pressure sensors, soil moisture sensors, relative humidity sensors, light sensors, and air circulation components.

12. The apparatus of claim 11, wherein said one or more interior sensor components are powered by a robotic arm assembly power source.

13. The apparatus of claim 1, wherein each of said plurality of robotic arm assemblies is comprised of a plurality of pivotal segments operatively coupled with mechanical actuators which actuate movement of said robotic arm assemblies when a signal is received from said one or more robotic arm controllers.

14. The apparatus of claim 1, which further includes a user interface that receives updated parameters to modify instructions implemented by said one or more robotic arm controllers.

15. The apparatus of claim 14, wherein said user interface receives a second set of updated parameters to modify instructions implemented by said conveyance valve controller.

16. The apparatus of claim 14, wherein said user interface receives user defined test parameter input to create testing session objects.

17. The apparatus of claim 16, wherein said user defined test parameter input is selected from a group consisting of: total distance traveled d, elevation y, distance x, uniform sampling interval T1, uniform sampling duration interval T2, gas type, source, chamber characteristics, test site characteristics, and test site terrain.

18. The apparatus of claim 16, wherein said testing session objects are virtual processing components that define chamber movement paths of said plurality of robotic arm assemblies corresponding to said user defined test parameter input.

19. The apparatus of claim 16, wherein said testing session objects define sampling intervals, sampling duration, chamber type selection criteria, and test session duration.

20. A method for sampling greenhouse gases, comprised of the steps of:
- securing a plurality of selectively attachable chambers to a plurality of robotic arm assemblies and a plurality of conveyance valves;
- iteratively receiving updated parameters to control at least one movement path for said plurality of robotic arm assemblies;
- iteratively receiving updated parameters to open and close each of said plurality of conveyance valves;
- translating each of said at least one movement path to path parameters;
    - wherein said path parameters are comprised of total distance traveled d, elevation y, and distance x;
- receiving uniform sampling interval T1;
- receiving uniform sampling duration interval T2;
- translating said d, x, y, T1, and T2 parameters to a quasi-unique sequence of path command signals to send to said one or more robotic arm controllers;
- initializing movement functions; and
- executing sample collection.

* * * * *